US012564457B2

(12) United States Patent
    Kumar et al.

(10) Patent No.: US 12,564,457 B2
(45) Date of Patent: Mar. 3, 2026

(54) ROBOTIC SURGICAL INSTRUMENTS

(71) Applicant: Covidien LP, Mansfield, MA (US)

(72) Inventors: Sunny Kumar, Hyderabad (IN);
               Arifmohamad Hamaju Mujawar,
               Sangli (IN); Rajat R. Rokde, Pune
               (IN); Naveen Kanth Nelli, Ambajipeta
               (IN); Tharageswari V, Erode (IN)

(73) Assignee: Covidien LP, Mansfield, MA (US)

( * ) Notice: Subject to any disclaimer, the term of this
              patent is extended or adjusted under 35
              U.S.C. 154(b) by 833 days.

(21) Appl. No.: 17/886,584

(22) Filed: Aug. 12, 2022

(65) Prior Publication Data

US 2023/0084874 A1      Mar. 16, 2023

Related U.S. Application Data

(60) Provisional application No. 63/243,808, filed on Sep.
     14, 2021.

(51) Int. Cl.
     *A61B 34/30*        (2016.01)
     *A61B 17/34*        (2006.01)
     *A61B 34/20*        (2016.01)
(52) U.S. Cl.
     CPC .......... *A61B 34/30* (2016.02); *A61B 17/3403*
         (2013.01); *A61B 2034/2057* (2016.02); *A61B*
         *2034/301* (2016.02); *A61B 2034/305* (2016.02)
(58) Field of Classification Search
     CPC ........ A61B 17/3403; A61B 2017/3405; A61B
            2017/3409; A61B 2034/301; A61B 34/30;
                                          A61B 2034/305
     See application file for complete search history.

(56) References Cited

U.S. PATENT DOCUMENTS 6,132,368  A     10/2000  Cooper
6,206,903  B1    3/2001   Ramans
                 (Continued)

FOREIGN PATENT DOCUMENTS

EP       3311755 A2     4/2018
WO       9529721 A1     11/1995
                 (Continued)

OTHER PUBLICATIONS

Extended European Search Report issued in corresponding appli-
cation EP 22195434 dated Jan. 27, 2023 (8 pages).
                 (Continued)

*Primary Examiner* — Quynh-Nhu H. Vu
(74) *Attorney, Agent, or Firm* — Carter, DeLuca & Farrel

(57)                ABSTRACT

A surgical robotic system includes a robotic arm having an
instrument drive unit. The surgical robotic system also
includes a surgical instrument that is coupled to the instru-
ment drive unit. The surgical instrument includes a hub
assembly with a hub housing and a longitudinal shaft
extending from the hub housing. The surgical instrument
also includes an end effector that is coupled to a distal end
portion of the longitudinal shaft. The end effector includes a
container with a composition (e.g., contrast dye or drug).
The end effector also includes a needle coupled to the
container and a sheath disposed over the needle and longi-
tudinally movable relative to the needle from an extended
position in which the needle is enclosed within the sheath to
a retracted position in which the needle extends out of the
sheath.

19 Claims, 9 Drawing Sheets

(56)  References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,860,878 B2 * | 3/2005 | Brock ............... A61B 5/415 606/1 |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |

(56) References Cited

U.S. PATENT DOCUMENTS

| | | | |
|---|---|---|---|
| 8,823,308 B2 | 9/2014 | Nowlin et al. | |
| 8,827,989 B2 | 9/2014 | Niemeyer | |
| 8,838,270 B2 | 9/2014 | Druke et al. | |
| 8,852,174 B2 | 10/2014 | Burbank | |
| 8,858,547 B2 | 10/2014 | Brogna | |
| 8,862,268 B2 | 10/2014 | Robinson et al. | |
| 8,864,751 B2 | 10/2014 | Prisco et al. | |
| 8,864,752 B2 | 10/2014 | Diolaiti et al. | |
| 8,903,546 B2 | 12/2014 | Diolaiti et al. | |
| 8,903,549 B2 | 12/2014 | Itkowitz et al. | |
| 8,911,428 B2 | 12/2014 | Cooper et al. | |
| 8,912,746 B2 | 12/2014 | Reid et al. | |
| 8,944,070 B2 | 2/2015 | Guthart | |
| 8,989,903 B2 | 3/2015 | Weir et al. | |
| 9,002,518 B2 | 4/2015 | Manzo | |
| 9,014,856 B2 | 4/2015 | Manzo et al. | |
| 9,016,540 B2 | 4/2015 | Whitman et al. | |
| 9,019,345 B2 | 4/2015 | O'Grady et al. | |
| 9,043,027 B2 | 5/2015 | Durant et al. | |
| 9,050,120 B2 | 6/2015 | Swarup et al. | |
| 9,055,961 B2 | 6/2015 | Manzo et al. | |
| 9,068,628 B2 | 6/2015 | Solomon et al. | |
| 9,078,684 B2 | 7/2015 | Williams | |
| 9,084,623 B2 | 7/2015 | Gomez et al. | |
| 9,095,362 B2 | 8/2015 | Dachs, II et al. | |
| 9,096,033 B2 | 8/2015 | Holop et al. | |
| 9,101,381 B2 | 8/2015 | Burbank et al. | |
| 9,113,877 B1 | 8/2015 | Whitman et al. | |
| 9,138,284 B2 | 9/2015 | Krom et al. | |
| 9,144,456 B2 | 9/2015 | Rosa et al. | |
| 9,198,730 B2 | 12/2015 | Prisco et al. | |
| 9,204,923 B2 | 12/2015 | Manzo et al. | |
| 9,226,648 B2 | 1/2016 | Saadat et al. | |
| 9,226,750 B2 | 1/2016 | Weir et al. | |
| 9,226,761 B2 | 1/2016 | Burbank | |
| 9,232,984 B2 | 1/2016 | Guthart et al. | |
| 9,241,766 B2 | 1/2016 | Duque et al. | |
| 9,241,767 B2 | 1/2016 | Prisco et al. | |
| 9,241,769 B2 | 1/2016 | Larkin et al. | |
| 9,259,275 B2 | 2/2016 | Burbank | |
| 9,259,277 B2 | 2/2016 | Rogers et al. | |
| 9,259,281 B2 | 2/2016 | Griffiths et al. | |
| 9,259,282 B2 | 2/2016 | Azizian et al. | |
| 9,261,172 B2 | 2/2016 | Solomon et al. | |
| 9,265,567 B2 | 2/2016 | Orban, III et al. | |
| 9,265,584 B2 | 2/2016 | Itkowitz et al. | |
| 9,283,049 B2 | 3/2016 | Diolaiti et al. | |
| 9,301,811 B2 | 4/2016 | Goldberg et al. | |
| 9,314,307 B2 | 4/2016 | Richmond et al. | |
| 9,317,651 B2 | 4/2016 | Nixon | |
| 9,345,546 B2 | 5/2016 | Toth et al. | |
| 9,393,017 B2 | 7/2016 | Flanagan et al. | |
| 9,402,689 B2 | 8/2016 | Prisco et al. | |
| 9,417,621 B2 | 8/2016 | Diolaiti | |
| 9,424,303 B2 | 8/2016 | Hoffman et al. | |
| 9,433,418 B2 | 9/2016 | Whitman et al. | |
| 9,439,648 B1 * | 9/2016 | Alhaqan | A61B 17/0469 |
| 9,446,517 B2 | 9/2016 | Burns et al. | |
| 9,452,020 B2 | 9/2016 | Griffiths et al. | |
| 9,474,569 B2 | 10/2016 | Manzo et al. | |
| 9,480,533 B2 | 11/2016 | Devengenzo et al. | |
| 9,503,713 B2 | 11/2016 | Zhao et al. | |
| 9,550,300 B2 | 1/2017 | Danitz et al. | |
| 9,554,859 B2 | 1/2017 | Nowlin et al. | |
| 9,566,124 B2 | 2/2017 | Prisco et al. | |
| 9,579,164 B2 | 2/2017 | Itkowitz et al. | |
| 9,585,641 B2 | 3/2017 | Cooper et al. | |
| 9,615,883 B2 | 4/2017 | Schena et al. | |
| 9,623,563 B2 | 4/2017 | Nixon | |
| 9,623,902 B2 | 4/2017 | Griffiths et al. | |
| 9,629,520 B2 | 4/2017 | Diolaiti | |
| 9,662,177 B2 | 5/2017 | Weir et al. | |
| 9,664,262 B2 | 5/2017 | Donlon et al. | |
| 9,675,354 B2 | 6/2017 | Weir et al. | |
| 9,687,312 B2 | 6/2017 | Dachs, II et al. | |
| 9,700,334 B2 | 7/2017 | Hinman et al. | |
| 9,718,190 B2 | 8/2017 | Larkin et al. | |
| 9,730,719 B2 | 8/2017 | Brisson et al. | |
| 9,737,199 B2 | 8/2017 | Pistor et al. | |
| 9,795,446 B2 | 10/2017 | DiMaio et al. | |
| 9,797,484 B2 | 10/2017 | Solomon et al. | |
| 9,801,690 B2 | 10/2017 | Larkin et al. | |
| 9,814,530 B2 | 11/2017 | Weir et al. | |
| 9,814,536 B2 | 11/2017 | Goldberg et al. | |
| 9,814,537 B2 | 11/2017 | Itkowitz et al. | |
| 9,820,823 B2 | 11/2017 | Richmond et al. | |
| 9,827,059 B2 | 11/2017 | Robinson et al. | |
| 9,830,371 B2 | 11/2017 | Hoffman et al. | |
| 9,839,481 B2 | 12/2017 | Blumenkranz et al. | |
| 9,839,487 B2 | 12/2017 | Dachs, II | |
| 9,850,994 B2 | 12/2017 | Schena | |
| 9,855,102 B2 | 1/2018 | Blumenkranz | |
| 9,855,107 B2 | 1/2018 | Labonville et al. | |
| 9,872,737 B2 | 1/2018 | Nixon | |
| 9,877,718 B2 | 1/2018 | Weir et al. | |
| 9,883,920 B2 | 2/2018 | Blumenkranz | |
| 9,888,974 B2 | 2/2018 | Niemeyer | |
| 9,895,813 B2 | 2/2018 | Blumenkranz et al. | |
| 9,901,408 B2 | 2/2018 | Larkin | |
| 9,918,800 B2 | 3/2018 | Itkowitz et al. | |
| 9,943,375 B2 | 4/2018 | Blumenkranz et al. | |
| 9,948,852 B2 | 4/2018 | Lilagan et al. | |
| 9,949,798 B2 | 4/2018 | Weir | |
| 9,949,802 B2 | 4/2018 | Cooper | |
| 9,952,107 B2 | 4/2018 | Blumenkranz et al. | |
| 9,956,044 B2 | 5/2018 | Gomez et al. | |
| 9,980,778 B2 | 5/2018 | Ohline et al. | |
| 10,008,017 B2 | 6/2018 | Itkowitz et al. | |
| 10,028,793 B2 | 7/2018 | Griffiths et al. | |
| 10,033,308 B2 | 7/2018 | Chaghajerdi et al. | |
| 10,034,719 B2 | 7/2018 | Richmond et al. | |
| 10,052,167 B2 | 8/2018 | Au et al. | |
| 10,085,811 B2 | 10/2018 | Weir et al. | |
| 10,092,344 B2 | 10/2018 | Mohr et al. | |
| 10,123,844 B2 | 11/2018 | Nowlin | |
| 10,188,471 B2 | 1/2019 | Brisson | |
| 10,201,390 B2 | 2/2019 | Swarup et al. | |
| 10,213,202 B2 | 2/2019 | Flanagan et al. | |
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,242 B2 | 7/2019 | Devengenzo et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald, II | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |

(56) References Cited

U.S. PATENT DOCUMENTS

| | | | |
|---|---|---|---|
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 2013/0023925 A1 | 1/2013 | Mueller | |
| 2018/0177558 A1* | 6/2018 | McKinley | A61B 34/00 |
| 2021/0137549 A1 | 5/2021 | Capart et al. | |
| 2021/0196251 A1 | 7/2021 | Dull | |

FOREIGN PATENT DOCUMENTS

| | | | | |
|---|---|---|---|---|
| WO | WO-2007022373 A2 * | 2/2007 | | A61B 5/15003 |
| WO | 2016210135 A1 | 12/2016 | | |

OTHER PUBLICATIONS

European Examination Report issued in corresponding application EP 22195434 dated Apr. 16, 2025.

* cited by examiner

ROBOTIC SURGICAL INSTRUMENTS

CROSS-REFERENCE TO RELATED APPLICATIONS

This application claims the benefit of and priority to U.S. Provisional Patent Application No. 63/243,808, filed on Sep. 14, 2021. The entire disclosure is incorporated by reference herein.

BACKGROUND

Technical Field

The present disclosure generally relates to a surgical robotic system having one or more modular arm carts each of which supports a robotic arm, and a surgical console for controlling the carts and their respective arms. More particularly, the present disclosure is directed to a surgical instrument couplable to and actuated by the robotic arm. The surgical instrument is configured to be used with interchangeable needle end effectors. The end effector may have a single use, exchangeable cartridge containing an injectable composition, such as a bioactive agent or a contrast agent. The end effector may be a needle-biopsy device.

Background of Related Art

Surgical robotic systems are currently being used in minimally invasive medical procedures. Some surgical robotic systems include a surgical console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body.

Injection of drugs in robotic procedures has been accomplished by using a long needle catheter which is typically held and controlled by a grasper device. Working with these catheters is somewhat challenging as the protruding catheter needle poses safety risks to users and inadvertent tissue contact inside the patient. An additional challenge is posed when passing the catheter needle through a laparoscopic port that contains pressure seals inside, since the needle may damage the seals.

These catheters are also used to inject indocyanine green (ICG) for marking or mapping tissue anatomy such as lymphatic drainage in near infrared (NIR) imaging. The utility of these catheters becomes even more problematic in robotic procedures. Any ICG ejected from the needle is detected by the NIR imaging camera and, as the leaked ICG spreads, its usefulness in marking and/or mapping tissue is lost. Thus, there is a need for injection devices for use with robotic surgical systems that avoid the deficiencies of conventional needle catheters manipulated by graspers.

SUMMARY

The present disclosure provides a surgical instrument usable with a surgical robotic system. The instrument includes a reusable hub assembly and a needle end effector. The reusable hub assembly is couplable to a surgical robotic arm, namely, to an instrument drive unit (IDU) of the robotic arm. The reusable hub assembly includes a longitudinal shaft coupled to a hub housing. The needle end effector is coupled to a distal end of the longitudinal shaft and is configured to hold a container having a composition, which may be a contrast agent or a bioactive agent. The needle end effector also includes an injection needle, a spring, and a retractable sleeve. The IDU is configured to retract the sleeve and inject the composition after position the injection needle within tissue. In particular, the reusable hub assembly also includes a piston shaft, which is configured to push the composition from the container to deliver the composition at a targeted tissue location in response to an actuation from the IDU. A second link is used to expose the needle covering sheath. A third link is used to articulate the disposable cartridge unit to get the needle into the right tissue plane.

According to one embodiment of the present disclosure, a surgical robotic system is disclosed. The surgical robotic system includes a robotic arm having an instrument drive unit. The surgical robotic system also includes a surgical instrument configured to couple to the instrument drive unit. The surgical instrument includes a hub assembly having: a hub housing; and a longitudinal shaft extending distally from the hub housing. The surgical instrument also includes an end effector releasably couplable to a distal end portion of the longitudinal shaft, the end effector including: a container including a composition. The end effector also includes a needle coupled to the container; and a sheath disposed over the needle and longitudinally movable relative to the needle from an extended position in which the needle is enclosed within the sheath to a retracted position in which at least a portion of the needle extends out of the sheath.

Implementations of the above embodiment may include one or more of the following features. According to one aspect of the above embodiment, the end effector may be articulatable relative to the longitudinal shaft from an unarticulated position to an articulated position. The end effector may include a distal joint and a proximal connector, the distal joint is pivotably coupled to the proximal connector via a distal pin. The hub assembly may include a first reciprocating link disposed within the longitudinal shaft. The end effector may further include an articulation link configured to mechanically engage a distal end portion of the first reciprocating link upon coupling of the end effector to the longitudinal shaft. The articulation link may be pivotably coupled to the proximal connector via a proximal pin, such that longitudinal movement of the articulation link articulates the end effector. The hub assembly may also include a longitudinally movable piston disposed within the longitudinal shaft. The end effector may also include a plunger configured to mechanically engage a distal end portion of the piston. The hub assembly may further include a second reciprocating link disposed within the longitudinal shaft. The end effector may also include a sheath link configured to mechanically engage a distal end portion of the second reciprocating link upon coupling of the end effector to the longitudinal shaft. Longitudinal movement of the sheath link articulates the end effector. The needle may be either straight or curved.

According to another embodiment of the present disclosure, a surgical instrument is disclosed. The surgical instrument includes a hub assembly having: a hub housing; and a longitudinal shaft extending distally from the hub housing. The surgical instrument also includes an end effector releasably couplable to a distal end portion of the longitudinal shaft, the end effector including: a container including a composition. The end effector also includes a needle coupled to the container; and a sheath disposed over the needle and longitudinally movable relative to the needle from an extended position in which the needle is enclosed within the sheath to a retracted position in which at least a portion of the needle extends out of the sheath.

Implementations may include one or more of the following features. According to one aspect of the above embodiment, the end effector may be articulatable relative to the longitudinal shaft from an unarticulated position to an articulated position. The end effector may include a distal joint and a proximal connector, the distal joint pivotably coupled to the proximal connector via a distal pin. The hub assembly may include a first reciprocating link disposed within the longitudinal shaft. The end effector may also include an articulation link configured to mechanically engage a distal end portion of the first reciprocating link upon coupling of the end effector to the longitudinal shaft. The articulation link may be pivotably coupled to the proximal connector via a proximal pin, such that longitudinal movement of the articulation link articulates the end effector. The hub assembly may further include a longitudinally movable piston disposed within the longitudinal shaft and the end effector includes a plunger configured to mechanically engage a distal end portion of the piston. The hub assembly may further include a second reciprocating link disposed within the longitudinal shaft and the end effector includes a sheath link configured to mechanically engage a distal end portion of the second reciprocating link upon coupling of the end effector to the longitudinal shaft, such that longitudinal movement of the sheath link articulates the end effector.

BRIEF DESCRIPTION OF THE DRAWINGS

Various embodiments of the present disclosure are described herein with reference to the drawings wherein.

DETAILED DESCRIPTION

Figure 1:
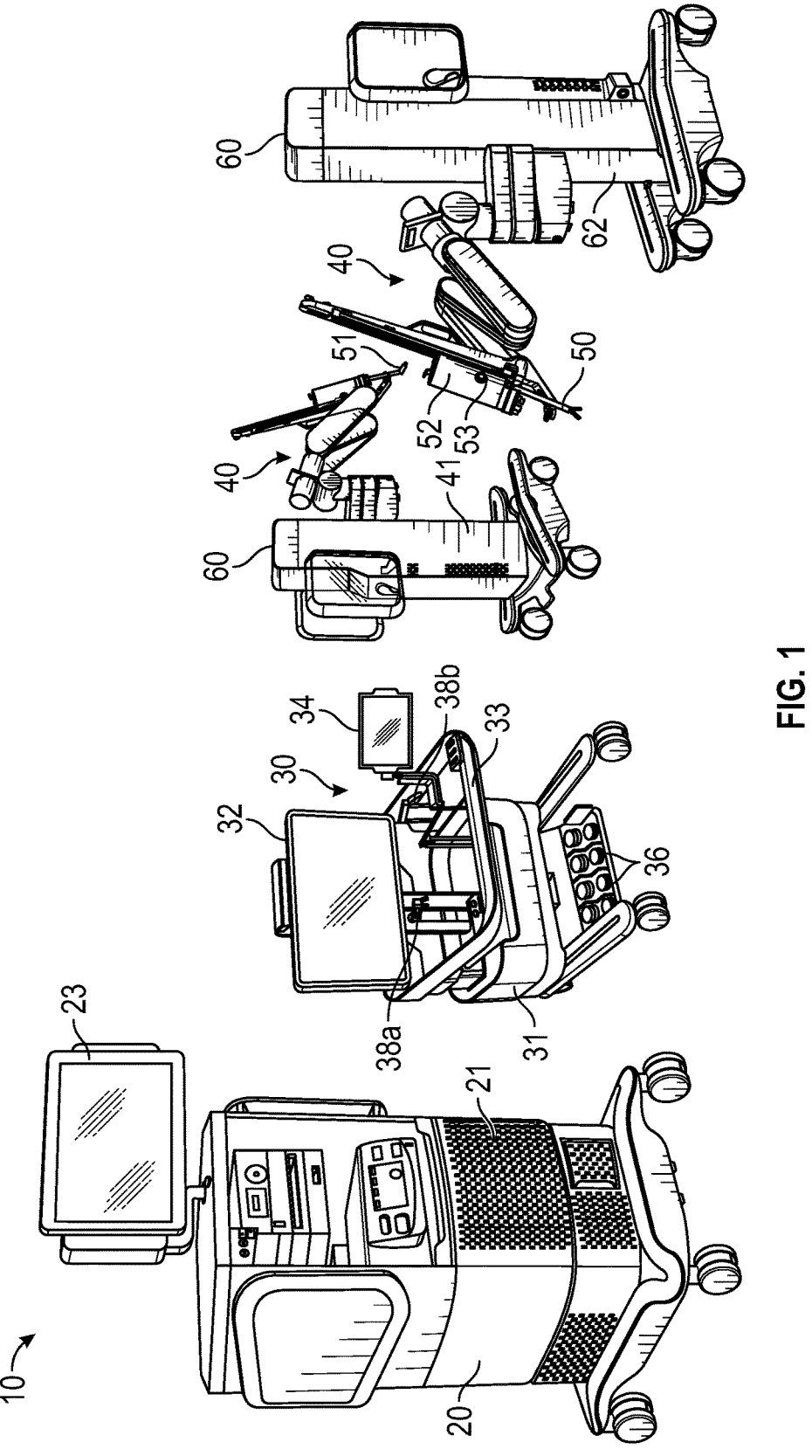
FIG. 1 is a schematic illustration of a surgical robotic system including a control tower, a console, and one or more surgical robotic arms according to an embodiment of the present disclosure.

Embodiments of the presently disclosed surgical robotic system are described in detail with reference to the drawings, in which like reference numerals designate identical or corresponding elements in each of the several views. As used herein the term "distal" refers to the portion of the surgical robotic system and/or the surgical instrument coupled thereto that is closer to the patient, while the term "proximal" refers to the portion that is farther from the patient.

The term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

As will be described in detail below, the present disclosure is directed to a surgical robotic system, which includes a surgical console, a control tower, and one or more movable carts having a surgical robotic arm coupled to a setup arm. The surgical console receives user input through one or more interface devices, which are interpreted by the control tower as movement commands for moving the surgical robotic arm. The surgical robotic arm includes a controller, which is configured to process the movement command and to generate a torque command for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgical console 30 and one or more robotic arms 40. Each of the robotic arms 40 includes a surgical instrument 50 removably coupled thereto. Each of the robotic arms 40 is also coupled to a movable cart 60.

The surgical instrument 50 is configured for use during minimally invasive surgical procedures. In embodiments, the surgical instrument 50 may be configured for open surgical procedures. In embodiments, the surgical instrument 50 may be an endoscope, such as an endoscopic camera 51, configured to provide a video feed for the user. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue.

One of the robotic arms 40 may include a camera 51 configured to capture video of the surgical site. The surgical console 30 includes a first display 32, which displays a video feed of the surgical site provided by camera 51 of the surgical instrument 50 disposed on the robotic arms 40, and a second display 34, which displays a user interface for controlling the surgical robotic system 10. The first and second displays 32 and 34 are touchscreens allowing for displaying various graphical user inputs.

The surgical console 30 also includes a plurality of user interface devices, such as foot pedals 36 and a pair of handle controllers 38*a* and 38*b* which are used by a user to remotely control robotic arms 40. The surgical console further includes an armrest 33 used to support clinician's arms while operating the handle controllers 38*a* and 38*b*.

The control tower 20 includes a display 23, which may be a touchscreen, and outputs on the graphical user interfaces (GUIs). The control tower 20 also acts as an interface between the surgical console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgical console 30, in such a way that robotic arms 40 and the surgical instrument 50 execute a desired movement sequence in response to input from the foot pedals 36 and the handle controllers 38*a* and 38*b*.

Each of the control tower 20, the surgical console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
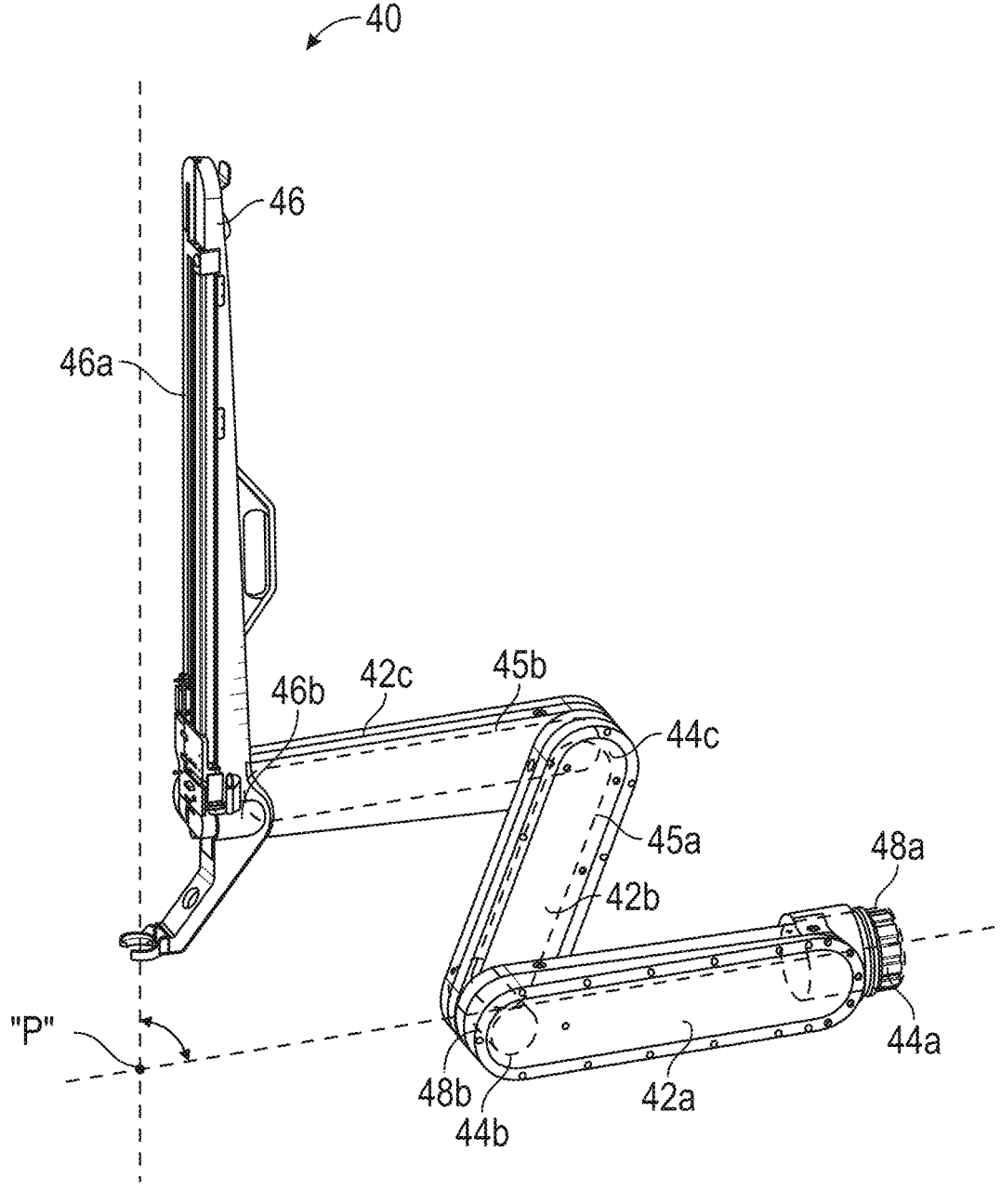
FIG. 2 is a perspective view of a surgical robotic arm of the surgical robotic system of FIG. 1 according to an embodiment of the present disclosure.
Figure 3:
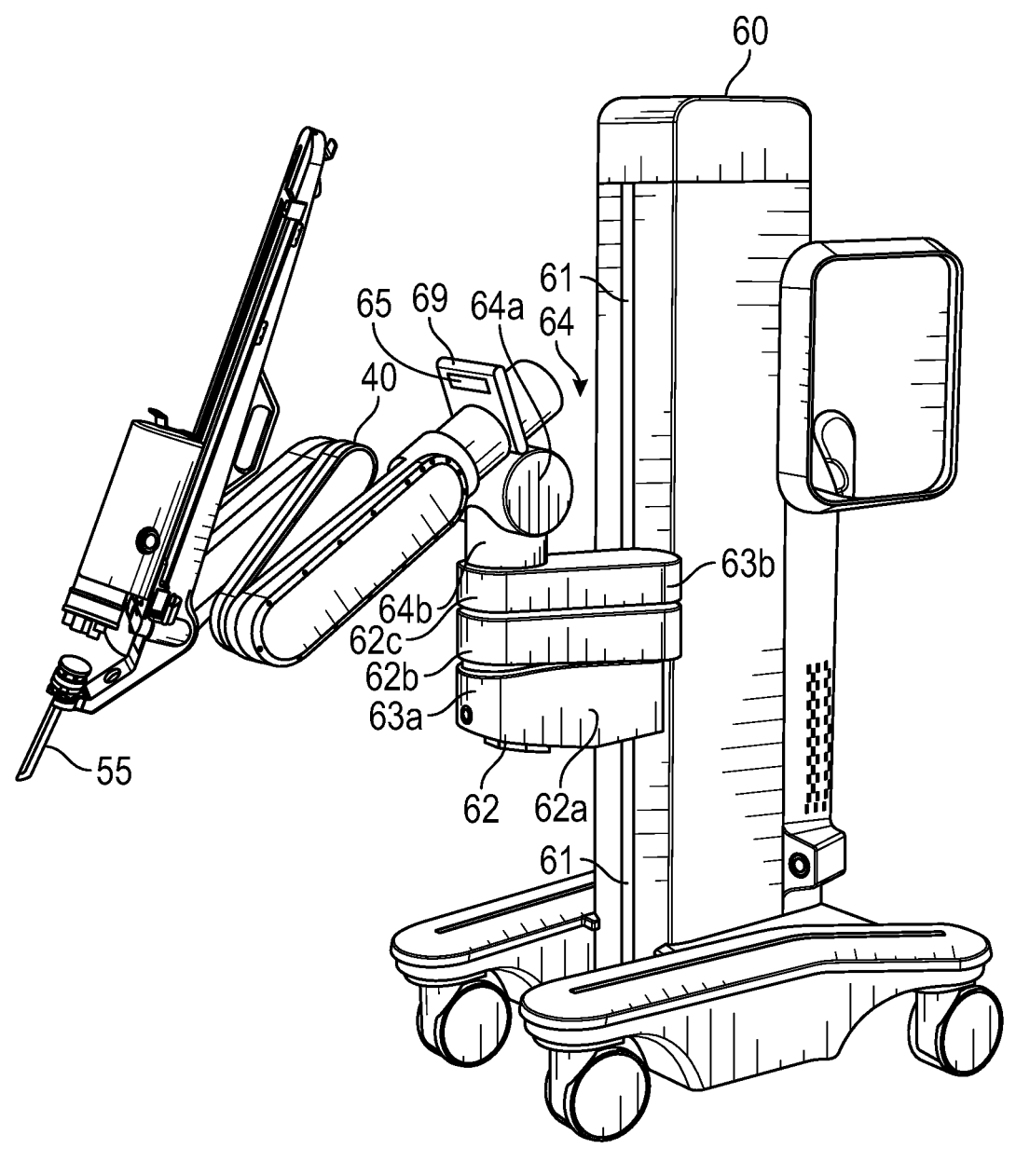
FIG. 3 is a perspective view of a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. The joint 44*a* is configured to secure the robotic arm 40 to the movable cart 60 and defines a first longitudinal axis. With reference to FIG. 3, the movable cart 60 includes a lift 61 and a setup arm 62, which provides a base for mounting of the robotic arm 40. The lift 61 allows for vertical movement of the setup arm 62. The movable cart 60 also includes a display 69 for displaying information pertaining to the robotic arm 40.

The setup arm 62 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 62 includes controls 65 for adjusting movement of the links 62*a*, 62*b*, 62*c* as well as the lift 61.

The third link 62*c* includes a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*c* via the belt 45*b*. Joint 44*c* may include a transfer case coupling the belts 45*a* and 45*b*, such that the actuator 48*b* is configured to rotate each of the links 42*b*, 42*c* and the holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the robotic arm 40 also includes a holder 46 defining a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components (e.g., end effector) of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42c. During endoscopic procedures, the instrument 50 may be inserted through an endoscopic port 55 (FIG. 3) held by the holder 46.

The robotic arm 40 also includes a plurality of manual override buttons 53 (FIGS. 1 and 5) disposed on the IDU 52 and the setup arm 62, which may be used in a manual mode. The user may press one or more of the buttons 53 to move the component associated with the button 53.

Figure 4:
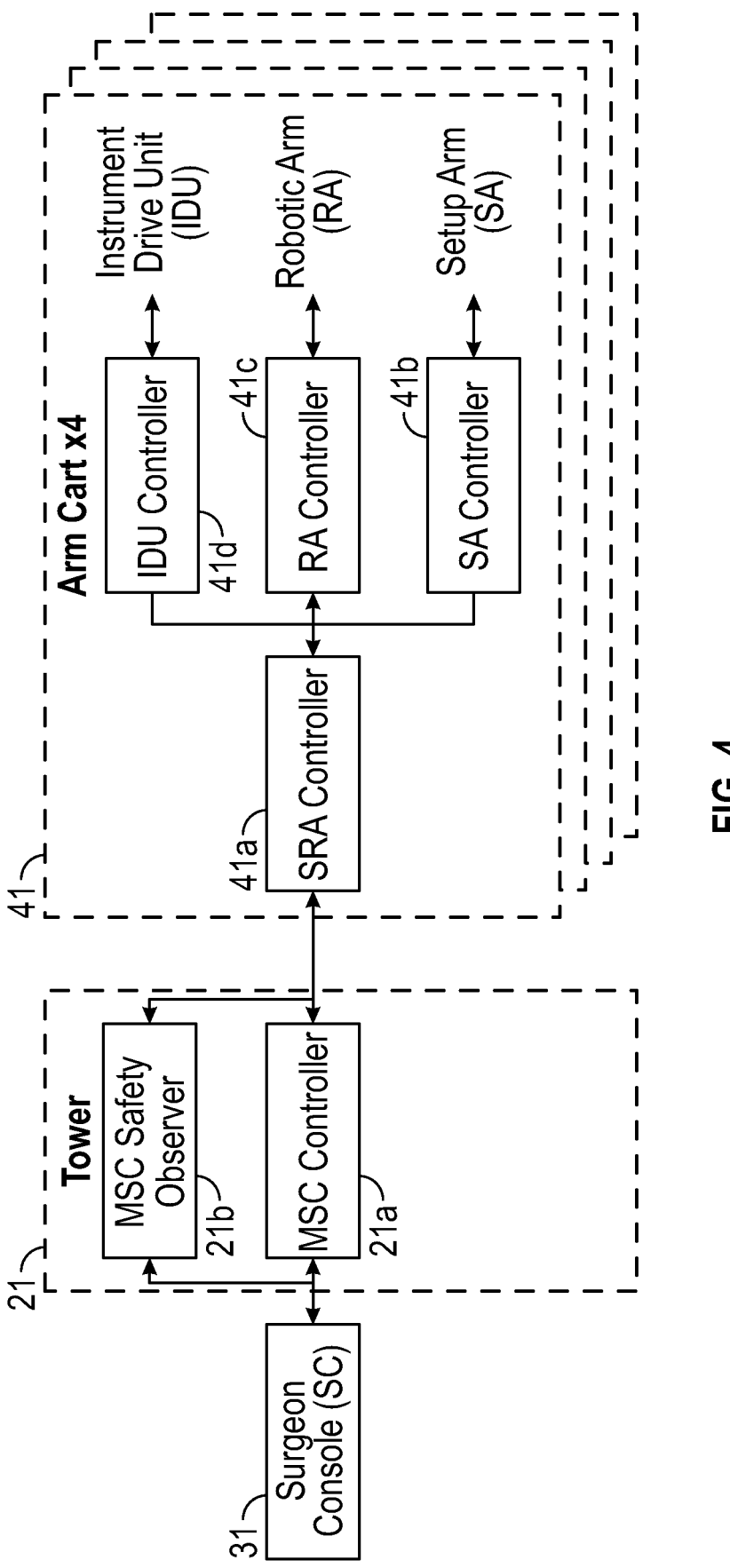
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgical console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgical console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

The setup arm controller 41b controls each of joints 63a and 63b, and the rotatable base 64 of the setup arm 62 and calculates desired motor movement commands (e.g., motor torque) for the pitch axis and controls the brakes. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controller 38a may be embodied as a coordinate position and role-pitch-yaw ("RPY") orientation relative to a coordinate reference frame, which is fixed to the surgical console 30. The desired pose of the instrument 50 is relative to a fixed frame on the robotic arm 40. The pose of the handle controller 38a is then scaled by a scaling function executed by the controller 21a. In embodiments, the coordinate position is scaled down and the orientation is scaled up by the scaling function. In addition, the controller 21a also executes a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
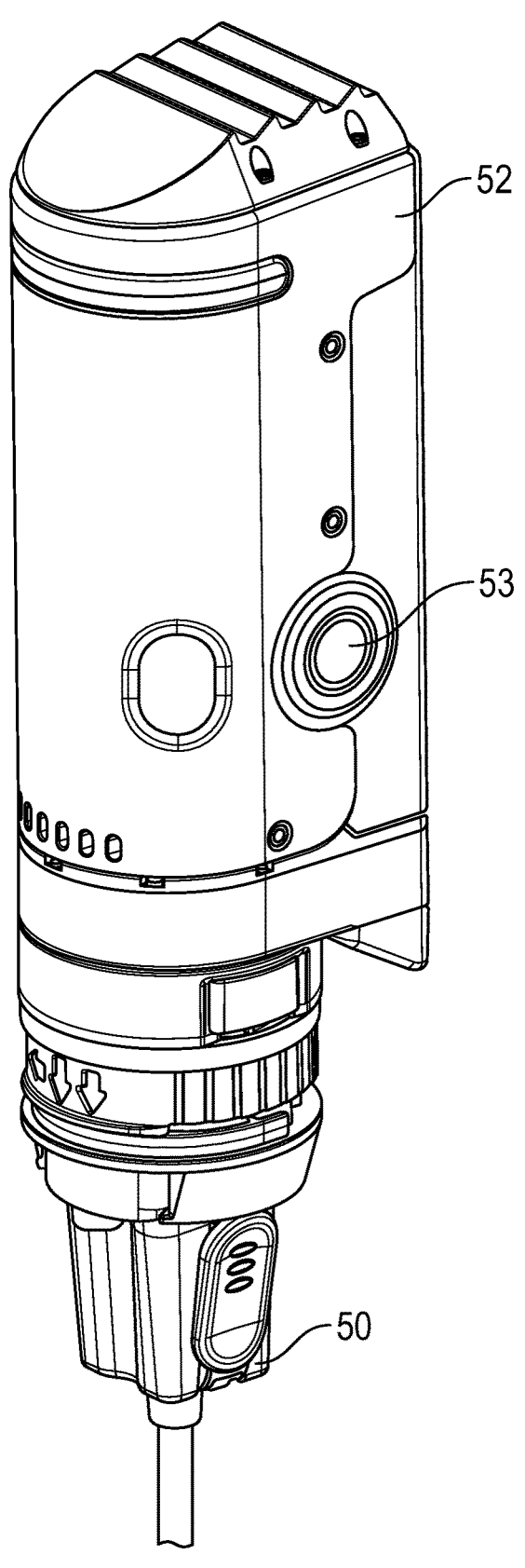
FIG. 5 is a perspective view of an instrument drive unit and a surgical instrument according to an embodiment of the present disclosure.
Figure 6:
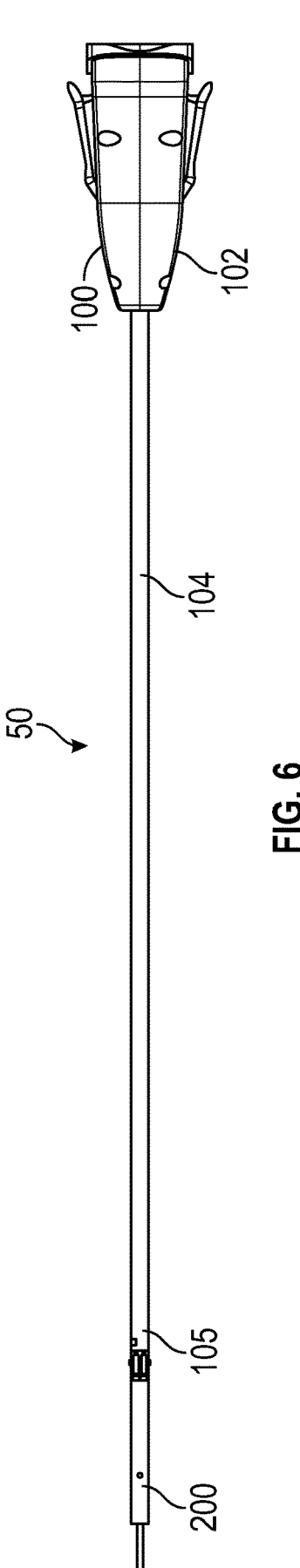
FIG. 6 is a side view of a surgical instrument according to an embodiment of the present disclosure.

With reference to FIGS. 5 and 6, the IDU 52 is shown in more detail and is configured to transfer power and actuation forces from its motors (not shown) to the instrument 50 to drive movement of components of the instrument 50, such as articulation, rotation, pitch, yaw, clamping, cutting, etc. The IDU 52 may also be configured for the activation or firing of an electrosurgical energy-based instrument or the like (e.g., cable drives, pulleys, friction wheels, rack and pinion arrangements, etc.).

Figure 7:
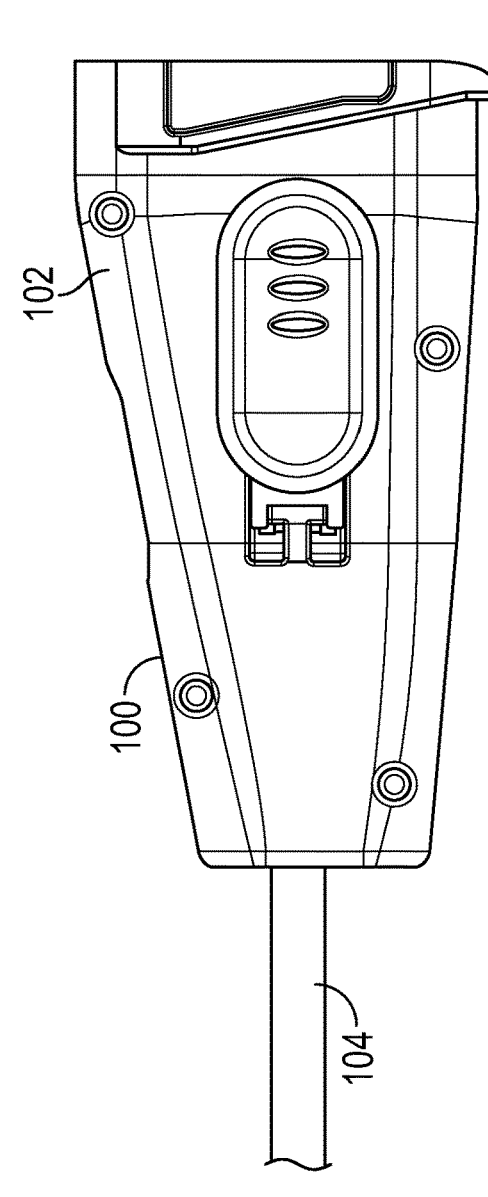
FIG. 7 is a side view of a proximal portion of the surgical instrument of FIG. 6, including a hub assembly according to an embodiment of the present disclosure.
Figure 8:
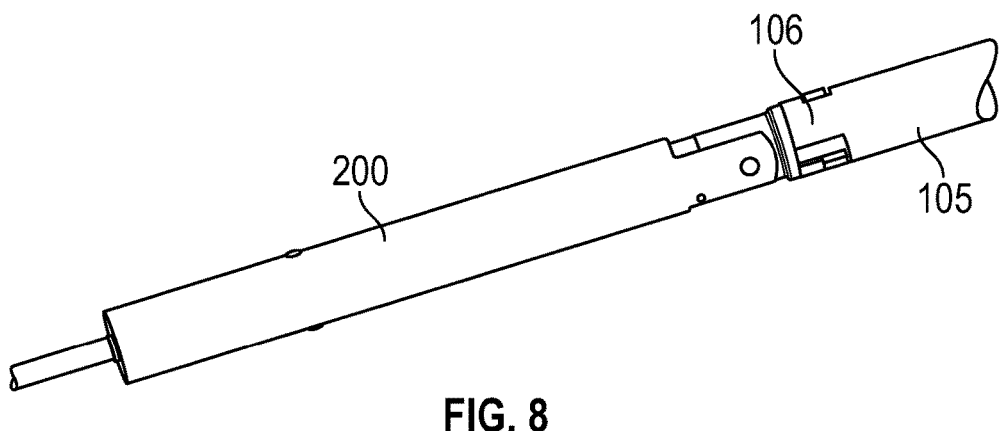
FIG. 8 is a perspective view of a distal portion of the surgical instrument of FIG. 6, including needle end effector according to an embodiment of the present disclosure.
Figures 10, 11:
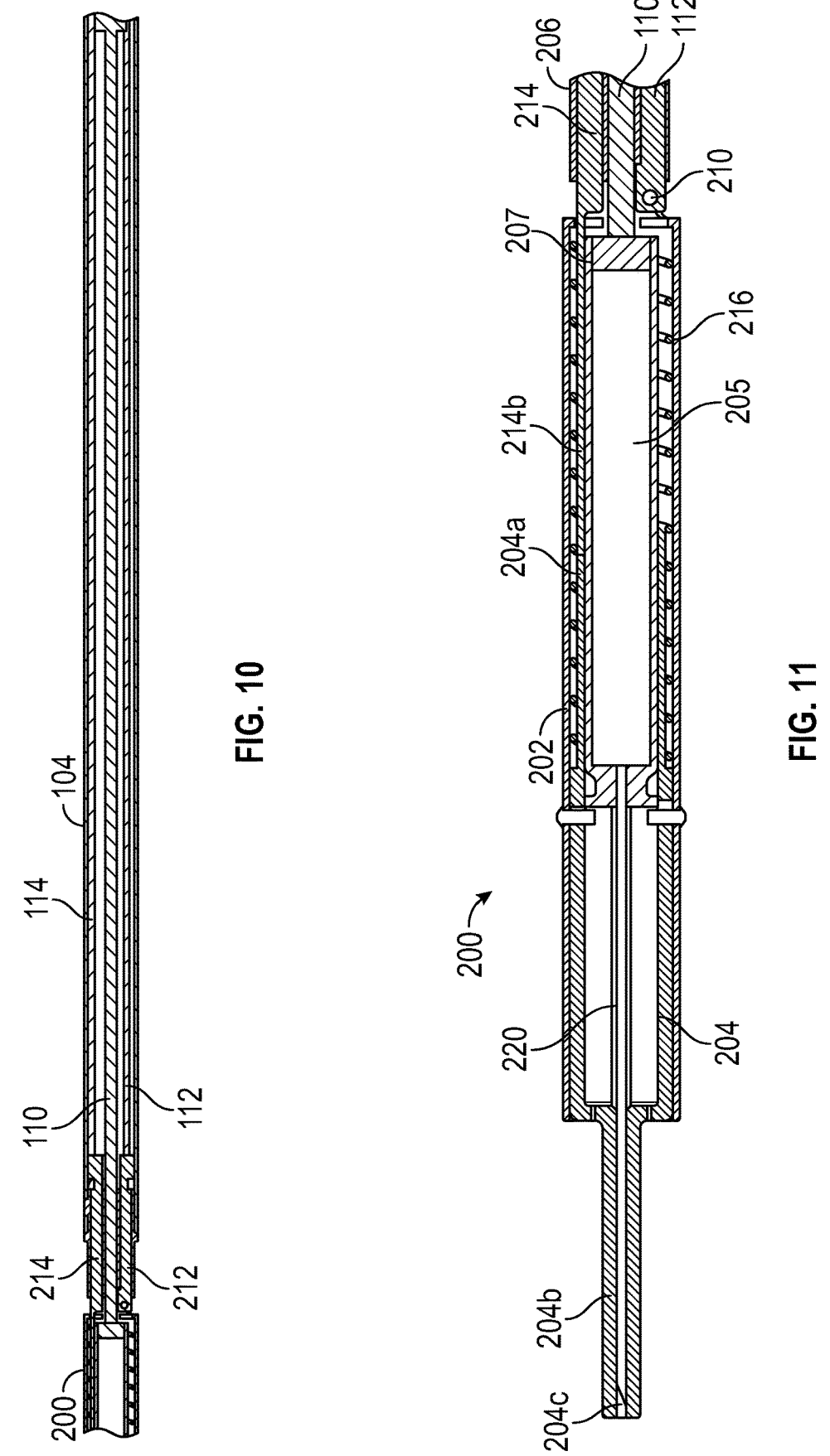
FIG. 10 is a cross-sectional view of a longitudinal shaft of the hub assembly of FIG. 7 according to an embodiment of the present disclosure.
FIG. 11 is a cross-sectional view of the needle end effector of FIG. 8 according to an embodiment of the present disclosure.

With reference to FIGS. 6 and 7, the instrument 50 includes a reusable hub assembly 100 having a hub housing 102 and a longitudinal shaft 104, which is coupled at its proximal end portion to the hub housing 102 and extends distally from the hub housing 102. The longitudinal shaft 104 defines a shaft longitudinal axis. The hub housing 102 is configured to couple to the IDU 52 and to engage the drive shafts (not shown) of the IDU 52. As shown in FIG. 10, the longitudinal shaft 104 houses various drive components for actuating a needle end effector 200, which is configured to releasably couple to the longitudinal shaft 104 of the hub assembly 100.

Figure 9:
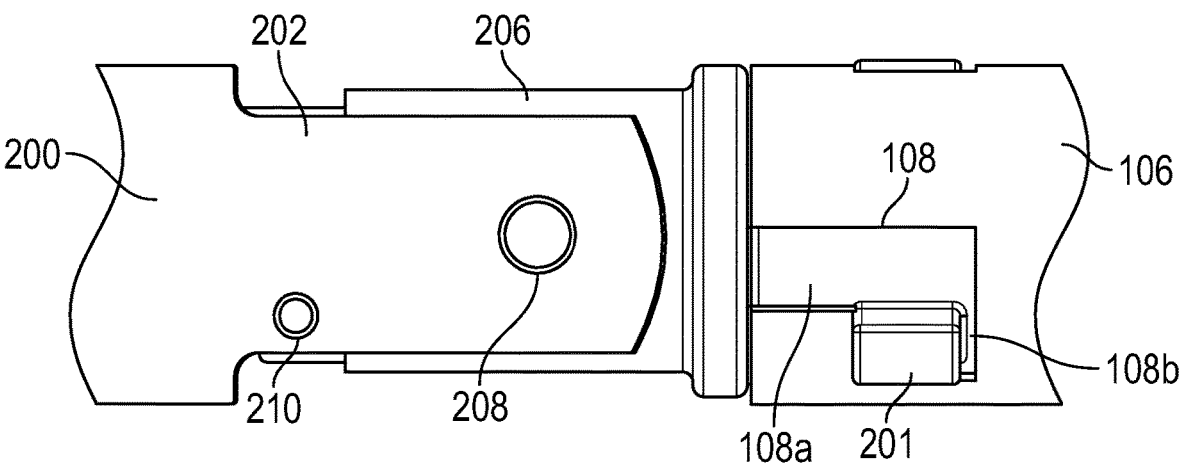
FIG. 9 is a side, enlarged view of a connection assembly between the hub assembly of FIG. 7 and the needle end effector of FIG. 8 according to an embodiment of the present disclosure.

With reference to FIG. 9, the longitudinal shaft 104 includes a distal connector 106 disposed at its distal end portion 105. The connector 106 includes a slot 108 having an insertion portion 108a parallel to the shaft longitudinal axis and a locking portion 108b transverse to the shaft axis. The slot 108 is configured to engage a protrusion 201 of the needle end effector 200 as the needle end effector 200 is initially inserted and then turned in the direction of the locking portion 108b to secure the needle end effector 200.

With reference to FIG. 10, the hub assembly 100 includes a piston 110, a first reciprocating link 112, and a second reciprocating link 114, each of which is disposed in the longitudinal shaft 104. The piston 110 may be centrally disposed within the longitudinal shaft 104 and the first and second reciprocating links 112 and 114 may be tubes, which are concentrically disposed around the piston 110. Each of the piston 110 and the first and second reciprocating links 112 and 114 are longitudinally and independently movable within the longitudinal shaft 104 and relative to the longitudinal shaft 104 and each other. Actuation of each of the piston 110 and the first and second reciprocating links 112 and 114 may be controlled by individual motors of the IDU 52.

Figure 12:
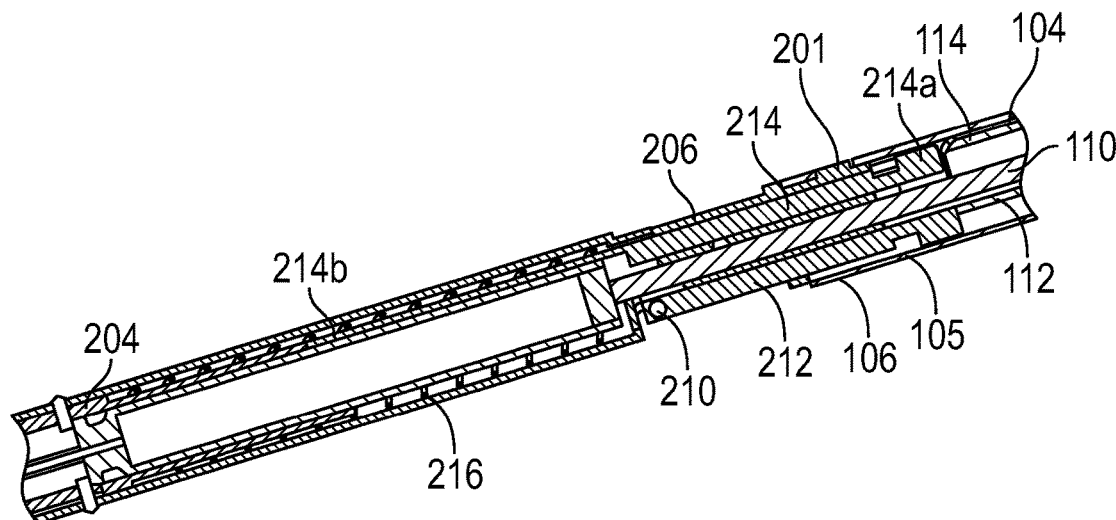
FIG. 12 is a cross-sectional view of the connection assembly of FIG. 9 according to an embodiment of the present disclosure.

With reference to FIGS. 11 and 12, the needle end effector 200 includes a distal joint 202, which encloses a needle sheath 204 and a container 205 having an injectable agent, which may be a contrast agent, such as ICG, or any suitable bioactive agent. Examples of classes of bioactive agents which may be utilized in accordance with the present disclosure include anti-adhesives, antimicrobials, analgesics, antipyretics, anesthetics, antiepileptic s, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

With reference to FIGS. 9 and 12, the needle end effector 200 also includes a proximal connector 206, which is configured to engage the distal connector 106 of the longitudinal shaft 104. The proximal connector 206 is configured to be inserted into the longitudinal shaft 104 and secured thereto via the engagement of the protrusion 201 to the slot 108.

With reference to FIGS. 9, 11, and 12, the distal joint 202 is pivotally coupled to the proximal connector 206 through a proximal pin 208. The distal joint 202 also includes an articulation link 212 and a distal pin 210, which is coupled to the articulation link 212 and the distal joint 202. Upon insertion of the needle end effector 200, the articulation link 212 is coupled to the first reciprocating link 112 such that longitudinal movement (either distally or proximally) of the first reciprocating link 112 moves the articulation link 212 in the same direction. As the articulation link 212 is moved proximally, the distal joint 202 is articulated relative to the longitudinal shaft 104 from an unarticulated position (e.g., 180°) to an articulated position (e.g., less than 180°). This is because the distal pin 210 is approximated to the proximal pin 208 as the articulation link 212 is moved proximally, thereby articulating the distal joint 202.

With reference to FIGS. 11 and 12, the distal joint 202 also includes a sheath link 214 having a distal end portion 214a, which is coupled to a proximal end portion 204a of the needle sheath 204. The needle sheath 204 is biased in the distal direction by a spring 216, which is disposed within the distal joint 202. The needle sheath 204 is retracted by being moved in a proximal direction by the sheath link 214, which is coupled to the second reciprocating link 114 at a proximal end portion 214b of the sheath link 214. Thus, longitudinal movement (either distally or proximally) of the second reciprocating link 114 moves the sheath link 214 in the same direction.

The container 205 includes a needle 220, which is disposed within a distal end portion 204b of the needle sheath 204. The needle 220 may be of any suitable gauge, which may be from 27 gauge to 14 gauge. Similarly, the container 205 may be of any suitable size, which may be from about 5 cc to about 200 cc. The needle 220 is movable within a lumen 204c of the needle sheath 204 as the needle sheath

204 is moved within the distal joint 202. The container 205 includes a plunger 207, which is configured to engage the piston 110, which when moved in a distal direction is configured to eject the contents of the container 205 through the needle 220. The piston 110, the articulation link 212, and the sheath link 214 may be formed from a flexible material which allows for articulation of the needle end effector 200 relative to the longitudinal shaft 104.

Prior to using the instrument 50 a desired needle end effector 200 is coupled to the reusable hub assembly 100. The instrument 50 is then coupled to the IDU 52 and is inserted into the endoscopic port 55, with the needle end effector 200 being in an unarticulated position and the needle sheath 204 being fully closed, concealing the needle 220. This allows the instrument 50 to be inserted through the endoscopic port 55 and to the surgical site without damaging the endoscopic port 55 or surrounding tissue. Once the needle end effector 200 is in position, the needle end effector 200 may be articulated and/or the instrument 50 may be rotated or moved to achieve a desired alignment of the needle end effector 200 with the tissue. Thereafter, the needle sheath 204 is retracted to expose the needle 220, which is then inserted into the tissue. The piston 110 is actuated to inject a desired amount of the contents of the container 205 into the tissue. Thereafter, the needle 220 is withdrawn from the tissue and the needle sheath 204 may be extracted in the distal direction to conceal the needle 220 to prevent any inadvertent contact with the tissue.

Figure 13:
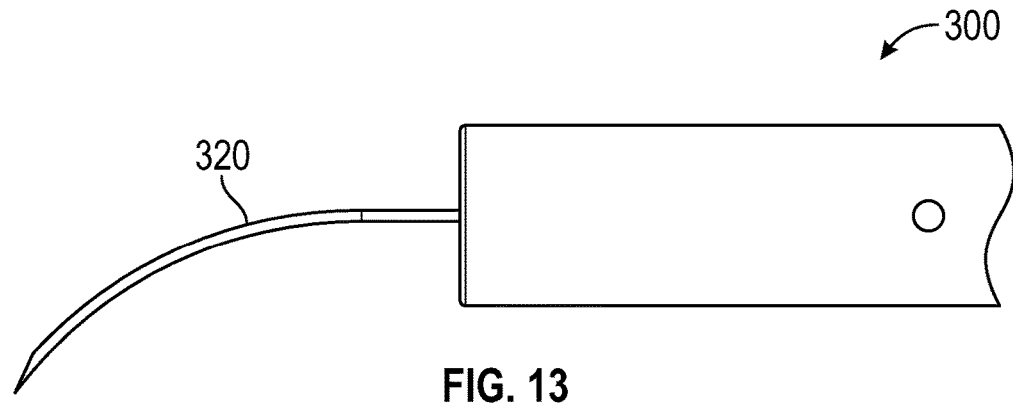
FIG. 13 is a side view of a biopsy end effector for use with the surgical instrument of FIG. 6 according to an embodiment of the present disclosure.
Figure 14:
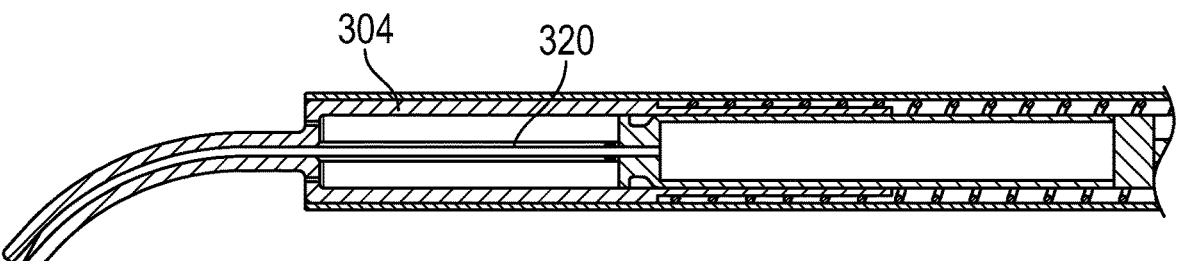
FIG. 14 is a cross-sectional, side view of the biopsy end effector of FIG. 13 according to an embodiment of the present disclosure.

With reference to FIGS. 13 and 14, another embodiment of a needle end effector 300 is shown, which is substantially like the needle end effector 200 except for the differences described in further detail below. The needle end effector 300 includes a curved needle 320 and a curved needle sheath 304. The curved needle 320 may be flexible to allow for the curved needle 320 to travel within the curved needle sheath 304. In further embodiments, either of the needle end effectors 200 and 300 may be used to perform needle biopsies by inserting the needles 200 and 300 into the tissue and rotating the instrument to secure a tissue sample within the needle.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:
a robotic arm including an instrument drive unit; and
a surgical instrument configured to couple to the instrument drive unit, the surgical instrument including:
a hub assembly including:
a hub housing; and
a longitudinal shaft extending distally from the hub housing; and
an end effector releasably couplable to a distal end portion of the longitudinal shaft, the end effector including:
a container including a composition;
a needle coupled to the container; and
a sheath disposed over the needle and longitudinally movable relative to the needle from an extended position in which the needle is enclosed within the sheath to a retracted position in which at least a portion of the needle extends out of the sheath.

2. The surgical robotic system according to claim 1, wherein the end effector is articulatable relative to the longitudinal shaft from an unarticulated position to an articulated position.

3. The surgical robotic system according to claim 2, wherein the end effector includes a distal joint and a proximal connector, the distal joint is pivotably coupled to the proximal connector via a distal pin.

4. The surgical robotic system according to claim 3, wherein the hub assembly includes a first reciprocating link disposed within the longitudinal shaft.

5. The surgical robotic system according to claim 4, wherein the end effector includes an articulation link configured to mechanically engage a distal end portion of the first reciprocating link upon coupling of the end effector to the longitudinal shaft.

6. The surgical robotic system according to claim 5, wherein the articulation link is pivotably coupled to the proximal connector via a proximal pin, such that longitudinal movement of the articulation link articulates the end effector.

7. The surgical robotic system according to claim 1, wherein the hub assembly includes a longitudinally movable piston disposed within the longitudinal shaft.

8. The surgical robotic system according to claim 7, wherein the end effector includes a plunger configured to mechanically engage a distal end portion of the piston.

9. The surgical robotic system according to claim 1, wherein the hub assembly includes a second reciprocating link disposed within the longitudinal shaft.

10. The surgical robotic system according to claim 9, wherein the end effector includes a sheath link configured to mechanically engage a distal end portion of the second reciprocating link upon coupling of the end effector to the longitudinal shaft.

11. The surgical robotic system according to claim 10, wherein longitudinal movement of the sheath link articulates the end effector.

12. The surgical robotic system according to claim 1, wherein the needle is either straight or curved.

13. A surgical robotic instrument comprising:
a hub assembly including:
a hub housing; and
a longitudinal shaft extending distally from the hub housing; and an end effector releasably couplable to a distal end portion of the longitudinal shaft, the end effector including:
a container including a composition;
a needle coupled to the container; and
a sheath disposed over the needle and longitudinally movable relative to the needle from an extended position in which the needle is enclosed within the sheath to a retracted position in which at least a portion of the needle extends out of the sheath.

14. The surgical robotic instrument according to claim 13, wherein the end effector is articulatable relative to the longitudinal shaft from an unarticulated position to an articulated position.

15. The surgical robotic instrument according to claim 14, wherein the end effector includes a distal joint and a proximal connector, the distal joint pivotably coupled to the proximal connector via a distal pin.

16. The surgical robotic instrument according to claim 15, wherein the hub assembly includes a first reciprocating link disposed within the longitudinal shaft.

17. The surgical robotic instrument according to claim 16, wherein the end effector includes an articulation link configured to mechanically engage a distal end portion of the first reciprocating link upon coupling of the end effector to the longitudinal shaft.

18. The surgical robotic instrument according to claim 17, wherein the articulation link is pivotably coupled to the proximal connector via a proximal pin, such that longitudinal movement of the articulation link articulates the end effector.

19. The surgical robotic instrument according to claim 13, wherein the hub assembly includes:
a longitudinally movable piston disposed within the longitudinal shaft and the end effector includes a plunger configured to mechanically engage a distal end portion of the piston; and
a second reciprocating link disposed within the longitudinal shaft and the end effector includes a sheath link configured to mechanically engage a distal end portion of the second reciprocating link upon coupling of the end effector to the longitudinal shaft, such that longitudinal movement of the sheath link articulates the end effector.

* * * * *